(12) United States Patent
Jung et al.

(10) Patent No.: US 11,311,253 B2
(45) Date of Patent: Apr. 26, 2022

(54) COLLIMATOR FOR RADIATION GENERATING APPARATUS

(71) Applicant: HANSEO UNIVERSITY ACADEMIC COOPERATION FOUNDATION, Seosan-si (KR)

(72) Inventors: Hong-Ryang Jung, Gwangmyeong-si (KR); Cheong-Hwan Lim, Suwon-si (KR); In Seog Kang, Incheon (KR); Ki-Jeong Kim, Gimpo-si (KR)

(73) Assignee: HANSEO UNIVERSITY ACADEMIC COOPERATION FOUNDATION, Seosan-si (KR)

( * ) Notice: Subject to any disclaimer, the term of this patent is extended or adjusted under 35 U.S.C. 154(b) by 23 days.

(21) Appl. No.: 17/101,352

(22) Filed: Nov. 23, 2020

(65) Prior Publication Data

US 2021/0153822 A1 May 27, 2021

(30) Foreign Application Priority Data

Nov. 26, 2019 (KR) .......................... 10-2019-0153402

(51) Int. Cl.
*A61B 6/06* (2006.01)
*A61B 6/00* (2006.01)
*A61B 6/10* (2006.01)

(52) U.S. Cl.
CPC ................ *A61B 6/06* (2013.01); *A61B 6/107* (2013.01); *A61B 6/54* (2013.01)

(58) Field of Classification Search
CPC ........... A61B 6/06; A61B 6/4007; A61B 6/54; A61B 6/107; A61N 2005/1094; G21F 1/085; G21K 1/046
See application file for complete search history.

(56) References Cited

U.S. PATENT DOCUMENTS

2017/0256329 A1* 9/2017 Kwerreveld ........... G21K 1/046

FOREIGN PATENT DOCUMENTS

| JP | 2006058174 A | 3/2006 |
| KR | 101364339 B1 | 2/2014 |
| KR | 1020160124535 A | 10/2016 |

* cited by examiner

*Primary Examiner* — Don K Wong
(74) *Attorney, Agent, or Firm* — Gearhart Law LLC; David Postolski, Esq.

(57) ABSTRACT

The present disclosure relates to a collimator for radiation generating apparatus, attached to a radiation generating apparatus, the collimator comprising: a frame fixed to the radiation generating apparatus and formed in a ring shape; and a shielding adjustment part provided with a plurality of shielding wings, one end of the shielding wings being hinged to the frame such that, when rotated, the other end of the shielding wings enters into a center of the frame, and the each one end of the shielding wings being disposed to be spaced apart on the frame, wherein the shielding wing is made of a radiation shielding metal. Accordingly, it is possible to easily adjust the diameter of radiation field made in a circular shape.

6 Claims, 5 Drawing Sheets

COLLIMATOR FOR RADIATION GENERATING APPARATUS

This application claims priority to Koran application No. 10-2019-0153402, filed Nov. 26, 2019, the contents of which are hereby fully incorporated by reference in their entirety.

1. FIELD

The present disclosure relates to a collimator for radiation generating apparatus, and more particularly, to a collimator for radiation generating apparatus, capable of adjusting the diameter of a circular radiation field.

2. BACKGROUND

Medical radiographic imaging using radiation contributes greatly to the diagnosis and treatment of diseases.

However, in addition to the useable function described above, medical radiation has a problem that it may cause disabilities due to exposure.

One of the most basic ways to reduce the amount of medical radiation exposure is to reduce the size of radiation field. Reducing the size of radiation field has an advantage of not only reducing the entrance surface dose (ESD) but also increasing the contrast of images due to the reduced scattered rays.

Previously, to adjust the size of radiation field, images were photographed while appropriately replacing conical members of various sizes, or through a variable collimator having a rectangular opening.

However, replacing conical members of various sizes at each time of photographing causes inconvenience in the operation, and the variable collimator having a rectangular opening can increase the radiation exposure of the patient by photographing unnecessary parts when examining a circular region.

SUMMARY

Therefore, a purpose of the present disclosure is to resolve the problems of prior art, that is, to provide a collimator for radiation generating apparatus, that is easy to use and can minimize the radiation exposure of a patient.

The problem to be solved by the present disclosure is not limited to the above-mentioned problems, and other problems that are not mentioned will be clearly understood by those skilled in the art from the following description.

The aforementioned purpose is achieved by a collimator for radiation generating apparatus, attached to a radiation generating apparatus, the collimator comprising: a frame fixed to the radiation generating apparatus and formed in a ring shape; and a shielding adjustment part provided with a plurality of shielding wings, one end of the shielding wings being hinged to the frame such that, when rotated, the other end of the shielding wings enters into a center of the frame, and the each one end of the shielding wings being disposed to be spaced apart on the frame, wherein the shielding wing is made of a radiation shielding metal.

It is desirable that two shielding adjustment parts are disposed to be spaced apart from each other on a central axis of the frame.

It is desirable that the shielding wing consists of a shielding part made of lead, positioned at a center of thickness of the shielding wing, and a reinforcement part made of aluminum, attached to both sides of the shielding part.

It is desirable that the shielding wing is made in an arc shape having a predetermined width.

It is desirable that the frame is made in a flat ring shape having a predetermined width.

It is desirable to further include an adjustment member having a flat ring shape, provided with a plurality of adjustment slits that are coupled rotatably with respect to the frame around a central axis of the frame, the adjustment slits extending in a radial direction and spaced apart in a circumferential direction, wherein the other end of the shielding wing is coupled to the adjustment member to be moveable and rotatable along the adjustment slit.

According to the collimator for radiation generating apparatus of the present disclosure, it is possible to easily adjust the size of radiation field by adjusting the angles of the shielding wings.

If each shielding wing is formed in an arc shape, the radiation field can be formed as close to a circular shape as possible.

Further, if the shielding adjustment part is formed in a dual form, it is possible to prevent penumbra from occurring.

If the shielding wing is formed of a shielding part made of lead and a reinforcement part made of aluminum, the shielding wing will not be easily deformed, and therefore, the shielding wing may rotate smoothly with respect to the frame.

When the collimator for radiation generating apparatus according to the present disclosure further has an adjustment member, it will be possible to rotate the shielding wings by a certain angle at once.

DETAILED DESCRIPTION

Hereinbelow, specific embodiments of the present disclosure will be described in detail with reference to the drawings attached.

The collimator for radiation generating apparatus according to the present disclosure 1 may be attached to the part that discharges radiation in a radiation generating apparatus, to play the role of adjusting the diameter of radiation field.

Figure 1:
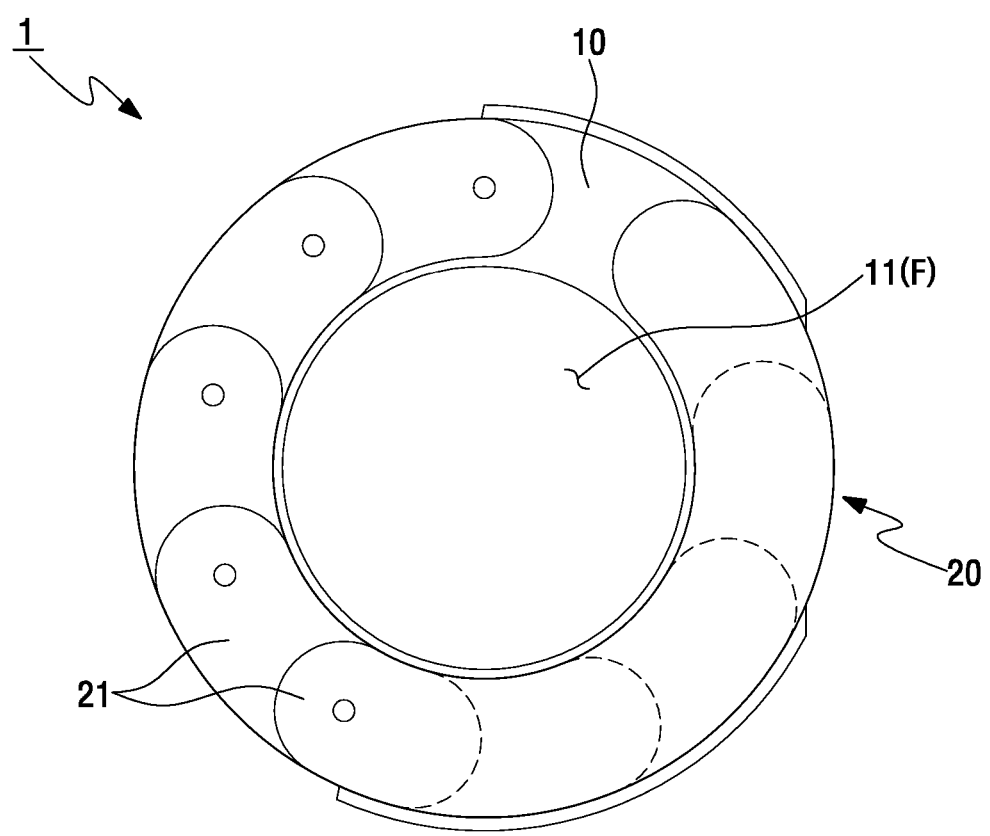
FIG. 1 is a plane view of a collimator for radiation generating apparatus according to the present disclosure.
Figure 2:
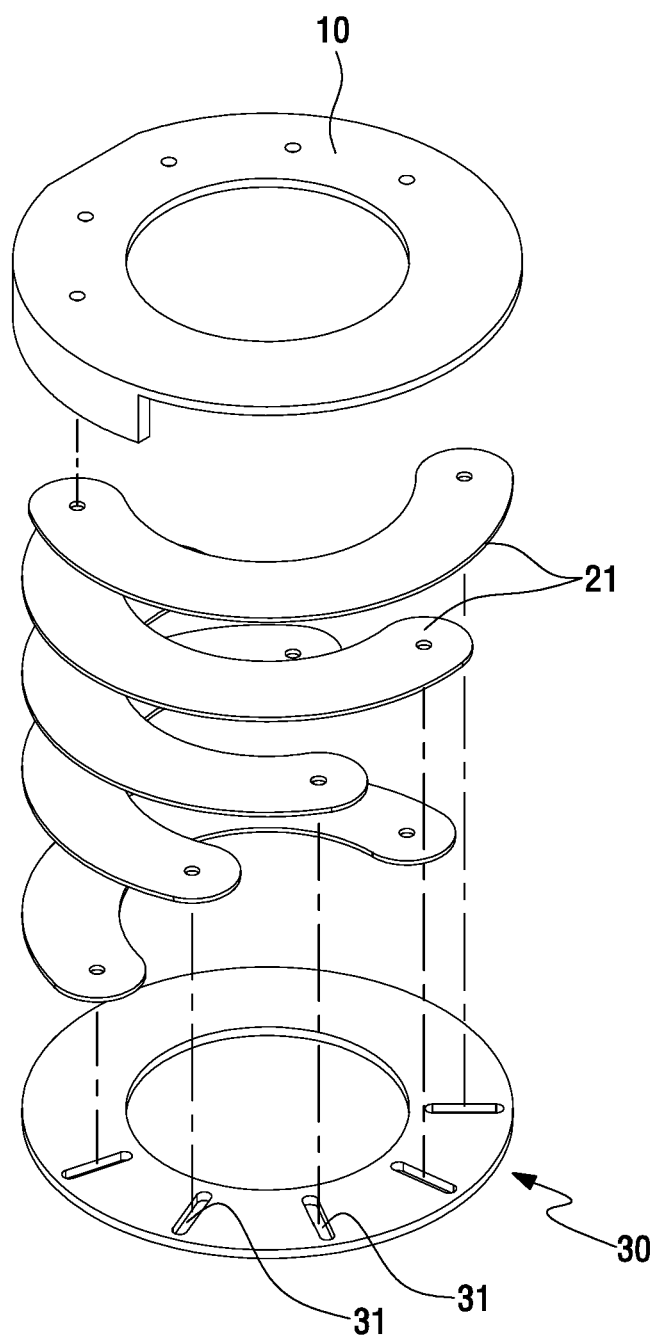
FIG. 2 is an exploded perspective view of the collimator for radiation generating apparatus according to the present disclosure.

In FIG. 1, a plane view of the collimator for radiation generating apparatus according to the present disclosure is illustrated, and in FIG. 2, an exploded perspective view of the collimator for radiation generating apparatus according to the present disclosure is illustrated.

The collimator for radiation generating apparatus according to the present disclosure 1 consists of a frame 10 and a shielding adjustment part 20.

The frame 10 is a member that is fixed to the radiation generating apparatus, and the overall shape of the frame 10 is a ring formed along the circumference of the part where the radiation is discharged. That is, the frame 10 is disposed such that the radiation generated by the radiation generating apparatus can be irradiated through a space 11 formed at the center of the frame 10.

The shielding adjustment part 20 has a plurality of shielding wings 21. Each shielding wing 21 is formed to have one end hinged to the frame 10 such that the other end of the shielding wing 21 can enter into the space 11 of the center of the frame 10, depending on the angle of the shielding wing 21 with respect to the frame 10. Further, the shielding wings 21 have one end spaced at regular intervals on the frame 10.

Figure 3A:
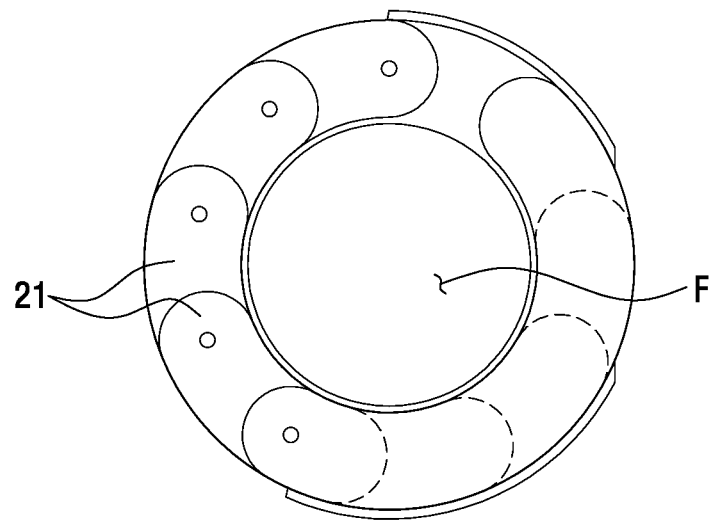
FIGS. 3A and 3B are an explanatory view of a method in which the collimator for radiation generating apparatus according to the present disclosure adjusts the size of radiation field.
Figure 3B:
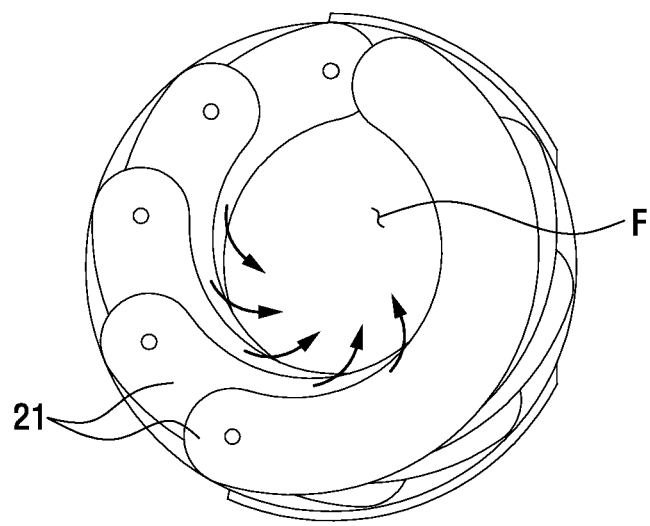

As illustrated in FIGS. 3A and 3B, the shielding adjustment part 20 can adjust the size of the hole through which the radiation passes, that is, the size of radiation field F, by adjusting the angle of the shielding wings 21 with respect to the frame 10. In other words, if the shielding wing 21 is not rotated with respect to the frame 10 as illustrated in FIG. 3A, the space 11 at the center of the frame 10 and the shielding wing 21 will not overlap each other, in which case the radiation field F will have a maximum size, and if the shielding wing 21 is rotated at a predetermined angle with respect to the frame 10 as illustrated in FIG. 3B, the other end of the shielding wing 21 will overlap with the space 11 at the center of the frame 10, thereby reducing the size of radiation field F.

Each shielding wing 21 is made of a high-density radiation shielding metal, such as lead, so as to shield radiation.

As described above, the collimator for radiation generating apparatus according to the present disclosure can easily adjust the size of radiation field by adjusting the angle of the shielding wings 21.

The shielding wing 21 may be formed in an arc shape having a predetermined width.

Since the inner circumference of the shielding wing 21 is formed in a curved shape, the hole formed by the inner circumference of the shielding wings 21 may be as close to a circular shape as possible, and accordingly, it is possible to prevent irradiation of radiation to unnecessary portions when inspecting circular portions.

FIG. 1 and the like illustrate a case where the collimator for radiation generating apparatus 1 of the present disclosure has five shielding wings 21, but it is also possible for the collimator for radiation generating apparatus 1 to have less than five or more than five shielding wings 21, and if the collimator for radiation generating apparatus 1 has more than five shielding wings 21, it is possible to form the hole formed by the shielding wings 21 in a shape more closer to a circle.

It is desirable that the frame 10 is formed in a flat ring shape having a predetermined width.

Due to the width of the frame 10, when the shielding wing 21 is not rotated with respect to the frame 10, the shielding wing 21 overlaps with the frame 10. Therefore, even when the shielding wing 21 is rotated with respect to the frame 10 at a predetermined angle in order to reduce the size of radiation field and the original position of the shielding wing 21 becomes empty, the frame 10 is able to prevent radiation from being irradiated through the original position of the shielding wing 21.

In order to shield radiation, the frame 10 may be made of a radiation shielding metal or may have a separate member made of a radiation shielding material.

Figure 4:
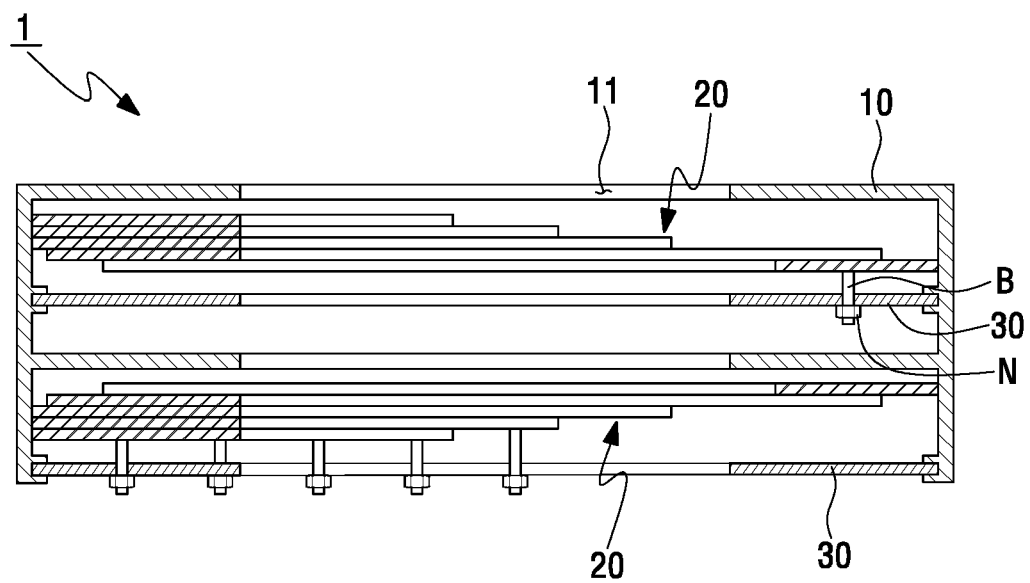
FIG. 4 is a cross-sectional view of the collimator for radiation generating apparatus according to the present disclosure.

As illustrated in FIG. 4, it is desirable that two shielding adjustment parts 20 are disposed apart on a central axis of the frame 10.

In this case, since the shielding adjustment part 20 doubles the shielding of radiation, it is possible to prevent penumbra from occurring.

Figure 5:
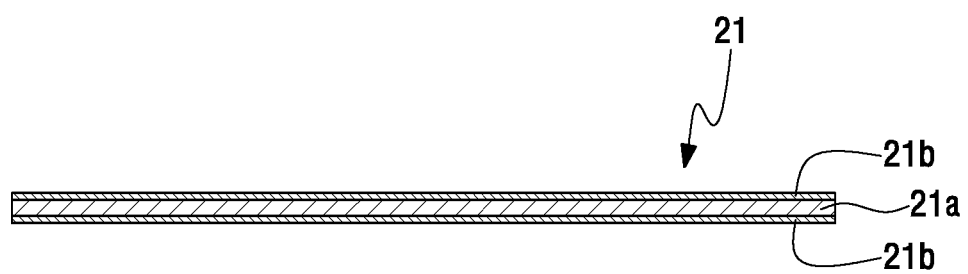
FIG. 5 is a cross-sectional view of a shielding wing constituting the collimator for radiation generating apparatus according to the present disclosure.

It is desirable that each shielding wing 21 consists of a shielding part 21a and a reinforcement part 21b. FIG. 5 illustrates a cross-sectional view of the shielding wing 21 in this case.

The shielding part 21a is positioned at the center of the thickness of the shielding wing 21, and as it is made of lead, it plays the role of shielding the radiation. Further, the reinforcement part 21b is made of an aluminum material, to be attached on both sides of the shielding part 21a, so that it can reinforce the lead having a high ductility.

Accordingly, the shielding wing 21 will not easily deform, and thus the shielding wing 21 can rotate smoothly with respect to the frame 10.

Since the aluminum forming the reinforcement part 21b has high rigidity but light weight, it is possible to prevent the weight of the shielding wing 21 from being increased by the reinforcement part 21b.

Figure 6A:
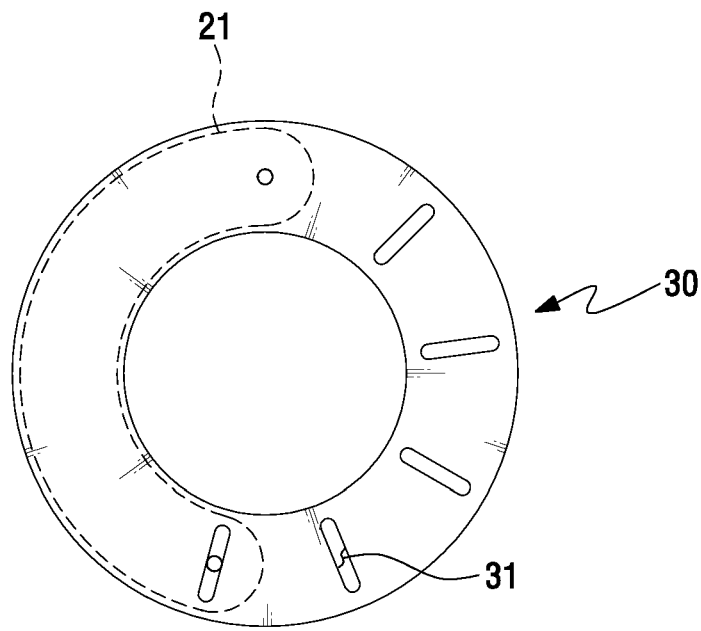
FIGS. 6A and 6B are an explanatory view of an adjustment member constituting the collimator for radiation generating apparatus according to the present disclosure.
Figure 6B:
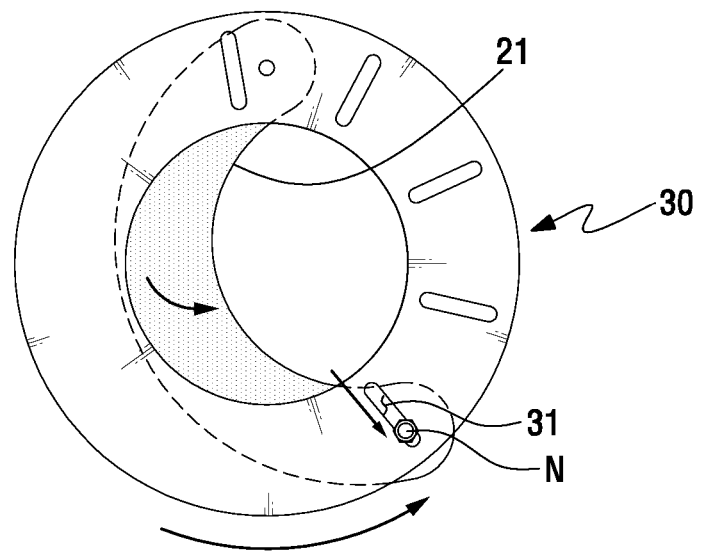

The collimator for radiation generating apparatus according to the present disclosure 1 may further include an adjustment member 30 in order to rotate each shielding wing 21. FIGS. 6A and 6B illustrates an explanatory view of the adjustment member 30.

The adjustment member 30 has an overall shape of a flat ring having a predetermined width, similar to the frame 10, and has a plurality of adjustment slits 31 that extend in a radial direction and that are spaced apart in a circumferential direction.

Such an adjustment member 30 is coupled rotatably with respect to the frame 10 around the central axis of the frame 10, and the other end of each shielding wing 21 is coupled with the adjustment member 30 such that it can move and rotate along each adjustment slit 31 of the adjustment member 30. For example, a long bolt B having a smaller diameter than the adjustment slit 31 is attached to each shielding wing 21, and as the long bolt passes through the adjustment slit 31 and fastens a nut N, the shielding wing 21 can be coupled to be movable and rotatable with respect to the adjustment slit 31 of the adjustment member. For reference, it is to be noted that FIGS. 6A and 6B illustrates that one shielding wing 21 is coupled with the adjustment member 30, but this is just for convenience of description, and thus in reality, each shielding wing 21 must be coupled per each adjustment slit 31.

As illustrated in FIG. 6A, when the coupling portion with the shielding wing 21 is located at the center of the slit 31 of the adjustment member 30, the shielding wing 21 will not rotate with respect to the frame 10, and thus it is possible to have a maximum radiation field, and as illustrated in FIG. 6B, when the adjustment member 30 is rotated to one direction, the other end of the shielding wings 21 will rotate with respect to the frame 10 along the adjustment member 30 as it move towards one end side of the adjustment slit 31, thereby reducing the size of radiation field. Further, on the contrary, when the adjustment member 30 is rotated to the other direction, the other end of the shielding wings 21 will rotate with respect to the frame along the adjustment member 30 as it moves towards the other end side of the adjustment slit 31, thereby increasing the size of radiation field again.

In other words, by rotating the adjustment member 30, the shielding wings 21 can be rotated at a certain angle all at once.

When there are two shielding adjustment parts 20, it is desirable that the adjustment member 30 is provided separately for each shielding adjustment part 20.

The scope of rights of the present disclosure is not limited to the embodiments described above, and the present disclosure can be implemented in various forms of embodiments within the claims set attached hereto. Without departing from the gist of the present disclosure claimed in the claims set, any person of ordinary skill in the art to which the present invention pertains is considered to be within the scope of the description of the claims of the present invention to various ranges that can be modified.

REFERENCE NUMERALS

1: COLLIMATOR FOR RADIATION GENERATING APPARATUS
10: FRAME
20: SHIELDING ADJUSTMENT PART
21: SHIELDING WING
21A: SHIELDING PART
21B: REINFORCEMENT PART
30: ADJUSTMENT MEMBER
31: ADJUSTMENT SLIT

What is claimed is:

1. A collimator for radiation generating apparatus, attached to a radiation generating apparatus, the collimator comprising:
    a frame fixed to the radiation generating apparatus and formed in a ring shape; and
    a shielding adjustment part provided with a plurality of shielding wings, one end of the shielding wings being hinged to the frame such that, when rotated, the other end of the shielding wings enters into a center of the frame, and the each one end of the shielding wings being disposed to be spaced apart on the frame,
    wherein the shielding wing is made of a radiation shielding metal.

2. The collimator for radiation generating apparatus according to claim 1,
    wherein two shielding adjustment parts are disposed to be spaced apart from each other on a central axis of the frame.

3. The collimator for radiation generating apparatus according to claim 1,
    wherein the shielding wing consists of a shielding part made of lead, positioned at a center of thickness of the shielding wing, and a reinforcement part made of aluminum, attached to both sides of the shielding part.

4. The collimator for radiation generating apparatus according to claim 1,
    wherein the shielding wing is made in an arc shape having a predetermined width.

5. The collimator for radiation generating apparatus according to claim 1,
    wherein the frame is made in a flat ring shape having a predetermined width.

6. The collimator for radiation generating apparatus according to claim 1,
    further comprising an adjustment member having a flat ring shape, provided with a plurality of adjustment slits that are coupled rotatably with respect to the frame around a central axis of the frame, the adjustment slits extending in a radial direction and spaced apart in a circumferential direction,
    wherein the other end of the shielding wing is coupled to the adjustment member to be moveable and rotatable along the adjustment slit.

\* \* \* \* \*